United States Patent [19]

Fujii et al.

[11] Patent Number: 6,002,048

[45] Date of Patent: Dec. 14, 1999

[54] FLUORINE-CONTAINING ETHER COMPOUND AND GELLING AGENT CONTAINING THE SAME

[75] Inventors: Yasuyuki Fujii; Eiko Tamura; Shinji Yano; Hisakazu Furugaki, all of Wakayama, Japan

[73] Assignee: Kao Corporation, Tokyo, Japan

[21] Appl. No.: 09/057,401

[22] Filed: Apr. 9, 1998

[30] Foreign Application Priority Data

Oct. 16, 1997 [JP] Japan ................................. 9-283650

[51] Int. Cl.⁶ ......................... C07C 41/00; C07C 43/11
[52] U.S. Cl. ................................. 568/579; 568/615
[58] Field of Search ..................... 568/615, 579

[56] References Cited

U.S. PATENT DOCUMENTS 5,914,430  6/1999  Fujii et al. .............................. 568/618

FOREIGN PATENT DOCUMENTS 0 753 500  1/1997  European Pat. Off. .

6-227942  8/1994  Japan .

*Primary Examiner*—Louise N. Leary
*Attorney, Agent, or Firm*—Oblon, Spivak, McClelland, Maier & Neustadt, P.C.

[57] ABSTRACT

A novel fluorine-containing compound having functions corresponding to those of fluorine is provided, which is stable under various conditions, excellent in compatibility with other solvents, and can be widely utilized as solvents, cosmetics, detergents, emulsifiers, surface finishing agents, lubricants, as well as lubricants or oils in the field of semiconductor/electronics.

That is, the present invention provides fluorine-containing ether compounds represented by the general formula (1):

$$Rf-(CH_2)_n-O-R^1 \qquad (1)$$

(wherein, Rf represents a straight or branched $C_{1-20}$ perfluoroalkyl group, $R^1$ represents a straight or branched $C_{11-20}$ alkyl group, n is a number from 1 to 8) and gelling agent containing the same.

9 Claims, No Drawings

FLUORINE-CONTAINING ETHER COMPOUND AND GELLING AGENT CONTAINING THE SAME

FIELD OF THE INVENTION

This invention relates to a novel fluorine-containing ether compound and a gelling agent containing it. More particularly, it relates to a novel fluorine-containing ether compound, an oil thereof and a gelling agent of organic solvents containing it which can be widely utilized as solvents, cosmetics, detergents, emulsifiers, surface finishing agents, lubricants, as well as lubricants or oils in the field of semiconductor/electronics, etc.

The present invention also relates to a process for production of the aforementioned fluorine-containing ether compounds.

DESCRIPTION OF PRIOR ART

Formerly, as general liquid oils used as oils for cosmetics, detergents, lubricants, etc., animal and vegetable or chemically synthesized esters (e.g., oils and fats) and hydrocarbons are known.

Desirable properties of such general liquid oils include, for example;

(1) having no smell and color;

(2) exhibiting no change in color and odor with time;

(3) excellent in touch;

(4) having appropriately low viscosity.

However, esters are not preferable because they may be hydrolyzed upon contact with water and have oily touch, while hydrocarbons are also undesirable because most of them have multi-branched structures, resulting in high viscosity although they are excellent in stability. Accordingly, none of the conventionally known liquid oils satisfy all of the above properties.

On the other hand, fluorine-containing organic compounds are known as oils for cosmetics, detergents, lubricants, etc. because they retain functions corresponding to those of fluorine, for example, water and oil repellency, low water absorption properties, electrical insulation properties, etc. Among them, for example, those having ester linkages have problems in hydrolysis resistance and those having polyoxyalkylene chain and perfluoropolyethers wherein all hydrogen atoms are substituted with fluorine atoms have problems in compatibility with other solvents, etc.

Accordingly, the object of the present invention is to provide novel fluorine-containing compounds which have functions of fluorine, and is stable under various conditions, and excellent in compatibility with other solvents, etc., and can be widely used as solvents, cosmetics, detergents, emulsifiers, surface finishing agents, lubricants, as well as lubricants or oils in the field of semiconductor/electronics.

JP-A 6-227942 describes decyl{2-(perfluorooctyl)ethyl}ether as a fluorine-containing ether compound. However, decyl{2-(perfluorooctyl)ethyl}ether is dissolved in most of solvents and oils excluding fluorine oil, but does not exhibit gelling ability.

DISCLOSURE OF THE INVENTION (Compound)

The present inventors have studied intensively to solve the above problems, and as the results, we have found novel fluorine-containing ether compounds and have attained the present invention.

That is, the present invention provides fluorine-containing ether compounds represented by the general formula (1)

wherein Rf represents a straight or branched $C_{1-20}$ perfluoroalkyl or fluoroalkyl group, $R^1$ represents a straight or branched $C_{11-20}$ alkyl group, and n is a number from 1 to 8.

In the fluorine-containing ether compounds of the present invention represented by the above general formula (1), Rf represents a straight or branched $C_{1-20}$ perfluoroalkyl or fluoroalkyl group, preferably a straight or branched $C_{4-20}$ perfluoroalkyl or fluoroalkyl group, particularly, a straight or branched $C_{8-20}$ perfluoroalkyl or fluoroalkyl group, more preferably, a $C_{10-20}$ perfluoroalkyl or fluoroalkyl group. $R^1$ represents a straight or branched $C_{11-20}$ alkyl group, and preferably a straight or branched $C_{12-18}$ alkyl group. n represents a number from 1 to 8, preferably 1 to 6, more preferably, 1 to 4, and particularly 2.

Rf of the formula (1) may be a perfluoroalkyl or a fluoroalkyl in which at least one hydrogen atom has been substituted by a fluorine atom. A mixture of both may be included in the invention.

(Process for Manufacturing)

The fluorine-containing ether compounds of the present invention represented by the above general formula (1) can be produced by reacting a fluorine-containing hydroxy compounds represented by the general formula (2):

(wherein, Rf and n are the same as defined above) with carbonyl compound of the general formula (3):

(wherein, $R^2$ and $R^3$ are the same or different to represent hydrogen atoms or $C_{1-20}$ alkyl groups, provided that the total carbon atoms of $R^2$ and $R^3$ are 10 to 19) or polymer thereof in the presence of a catalyst in an atmosphere of hydrogen (in hydrogen gas).

Fluorine-containing hydroxy compounds represented by the general formula (2) include, for example, $C_{1-8}$ straight-chain alcohols having a perfluoroalkyl group or a fluoroalkyl group wherein at least one hydrogen atom of a $C_{1-20}$ straight or branched alkyl group is substituted by a fluorine atom. Embodiments include, but are not limited to, straight fluorine-containing alcohols such as 2,2,3,3,3-pentafluoropropanol, 2-(perfluorohexyl)ethanol, 2-(perfluorooctyl)ethanol, 2-(perfluorodecyl)ethanol, 2-(perfluorododecyl)ethanol, 2-(perfluorotetradecyl)ethanol, 2-(perfluorohexadecyl)ethanol, 6-(perfluoroethyl)hexanol, 6-(perfluorobutyl)hexanol, 6-(perfluorohexyl)hexanol, 6 -(perfluorooctyl)hexanol, 2,2,3,4,4,4-hexafluorobutanol, 2,2,3,3-tetrafluoropropanol, 1H, 1H,5H-octafluoropentanol, 1H,1H,7H-dodecafluoroheptanol, 1H,1H, 9H-hexadecafluorononanol; branched fluorine-containing alcohols such as 2-(perfluoro-3-methylbutyl)ethanol, 2-(perfluoro-5-methylhexyl)ethanol, 2-(perfluoro-7-methyloctyl)ethanol, 2-(perfluoro-9-methyldodecyl)ethanol, 6-(perfluoro-1-methylethyl)hexanol, 2-(perfluoro-3-methylbutyl)hexanol, 6-(perfluoro-5-methylhexyl)hexanol, 6-(perfluoro-7-methyloctyl)hexanol. Among these fluorine-containing compounds, 2-(perfluorohexyl)ethanol, 2-(perfluorooctyl)ethanol, 2-(perfluorodecyl)ethanol and 2-(perfluorododecyl)ethanol are preferred.

Carbonyl compounds represented by the general formula (3) include, in addition to compounds having carbonyl groups, compounds easily converted with acid or heating to those having carbonyl groups.

Carbonyl compounds represented by the general formula (3) used in the present invention include, but are not limited to, undecylaldeyde, dodecylaldehyde, octadecylaldehyde, eicosylaldehyde, etc.

In the above process, charge ratio of fluorine-containing hydroxy compound to carbonyl compound is not particularly limited, but generally the ratio of fluorine-containing compound/carbonyl compound (by mole) is preferably 30/1 to 1/30. Particularly, 20/1 to 1/20, especially, 10/1 to 1/10 is preferred. If the fluorine-containing hydroxy compound has a low molecular weight and can be easily removed, it is preferable to use such an excess of the fluorine-containing hydroxy compound as to react a carbonyl compound completely. If fluorine-containing hydroxy compound has high molecular weight and further solidifies at ambient temperature, it is preferable to use an excess of carbonyl compound to completely react fluorine-containing hydroxy compound which may be hardly removed. The molar ratio of fluorine-containing hydroxy compound/carbonyl compound out of the above range has little effect on yield, but is not economical.

In the present invention, catalysts used for reaction of a fluorine-containing hydroxy compound with a carbonyl compound may not be particularly limited so long as they have hydrogenation ability, and include palladium catalyst; palladium compound such as palladium hydroxide, palladium oxide; ruthenium, rhodium or platinum catalyst; ruthenium oxide, rhodium oxide, platinum oxide, etc. Catalysts such as iridium, osmium, rhenium may also be used. These catalysts may be appropriately supported on carriers such as carbon, alumina, silica alumina, silica and zeolite. Among these catalysts, preferably palladium compounds, more preferably palladium catalysts, palladium hydroxide or palladium oxide, which is supported on carbon, alumina, silica alumina, silica or zeolite, most preferably, palladium catalysts supported on carbon, can be used.

In the present invention, catalysts may be generally used being supported on a carrier such as carbon, alumina at the ratio of 2 to 10% by weight, but they may be directly used instead of being supported on a carrier. Moreover, they may contain about 20 to 60% by weight of water.

Catalysts may be preferably used at 0.1 to 10% by weight based on fluorine-containing hydroxy compound or carbonyl compound to be used so long as they are those supported on a carrier at the ratio of 5% by weight based on the carrier. With less than 0.1% by weight of catalyst, reaction may proceed, but undesirably at slow rate. On the other hand, with more than 10% by weight of catalyst, reaction may proceed rapidly, but undesirably side reaction may proceed simultaneously. More preferably, the amount of catalyst is 0.5 to 5% by weight.

Catalysts may be used within any pH range, but preferably at pH 8 to 2, more preferably at pH 7.5 to 3. The term 'pH of catalyst' herein used means pH of an aqueous solution of catalyst powder (2 g) dispersed in ion exchanged water (30 g).

In the present invention, fluorine-containing compound and carbonyl compound are reacted in an atmosphere of hydrogen. The hydrogen pressure is not particularly limited, and the reaction may be carried out either at an increased pressure or at atmospheric pressure, preferably at 1 (atmospheric pressure) to 300 kg/cm$^2$, particularly preferably at 1 (atmospheric pressure) to 200 kg/cm$^2$.

When carbonyl compounds are aldehydes, it is preferable to carry out reaction by adding such aldehydes dropwise to the reaction system. Reaction is carried out by adding aldehydes dropwise to the reaction system, which prevents side reaction (aldol formation) of aldehydes, yielding fluorine-containing ether compound at high yield. In addition, amount of aldehydes to be added may be reduced. The reaction can be completed generally with 1 to 2 times equivalent of aldehyde based on fluorine-containing hydroxyl compound.

The way to add aldehyde dropwise to the reaction system may not be particularly limited, but it is preferable to continuously and/or intermittently add dropwise to the reaction system within 0.5 to 20 hours. The rate to add aldehyde may be suitably selected depending on the reaction scale. For 0.5 liter scale, for example, 0.1 to 180 g/hr is preferred and 0.6 to 60 g/hr is more preferred.

In the present invention, reaction temperature during reaction between fluorine-containing compound and carbonyl compound is not particularly limited, but preferably 10 to 200° C., particularly preferably 30 to 180° C.. The reaction time may be suitably selected depending on reaction temperature, hydrogen pressure, amount of catalyst, etc., and generally 1 to 24 hours, preferably 1 to 12 hours.

In the present reaction, the objective fluorine-containing ether compound as well as equimolar amount of water may be produced. It is preferable to carry out reaction while removing thus produced water, which preferably facilitates reaction. Examples of the method to remove water include, for example, to carry out reaction in the presence of a dehydrating agent to remove water, to flow gas such as hydrogen to remove water, to distill off water by azeotropic dehydration. Among them, the method is preferred wherein water is removed by carrying out reaction in the presence of a dehydrating agent or the method wherein water is removed using a flow of hydrogen. In particular, a method wherein water produced from the reaction as a by-product is removed from the system by flowing hydrogen using a reactor equipped with a dehydrating tube and only unreacted materials are recycled to the system.

In the method wherein reaction is carried out in the presence of a dehydrating agent, embodiments of such dehydrating agents used include anhydrous magnesium sulfate, anhydrous sodium sulfate, anhydrous calcium sulfate, anhydrous calcium chloride, molecular sieves, etc. Among them, anhydrous magnesium sulfate, anhydrous sodium sulfate are preferred, and anhydrous magnesium sulfate is most preferable. The amount of a dehydrating agent varies depending on types of the dehydrating agent to be used, and when anhydrous magnesium sulfate is used, 0.05 to 2 times mole, further 0.1 to 1 time mole based on the fluorine-containing hydroxy compound is preferred.

In the method wherein water is removed from the system with flowing hydrogen, the flow rate of hydrogen may be suitably selected depending on the reaction scale. For example 0.7 to 2100 ml/min. is preferable and 0.7 to 700 ml/min. is more preferable for 70 ml scale. Hydrogen may be flowed continuously or intermittently during the reaction, but continuous flow is preferred to smoothly conduct reaction. The hydrogen flowed through the reaction system may be directly released into air, but for efficient use of hydrogen, it is efficient and preferable to utilize the hydrogen released from the system for reaction by returning through a circulating line or the like and flowing again through the system and recycling again. Further, when unreacted materials are removed from the system simultaneously with water, it is preferable to return only unreacted materials to the system.

In the reaction according to the present invention, solvent which has no bad effect on the reaction may be sometimes used to carry out reaction. As such solvents having no bad effect on the reaction include, but are not limited to, hydrocarbon solvent such as hexane, heptane and octane.

When a solvent having no bad effect on the reaction is used, the amount of such a solvent to be used is not particularly limited, but preferably 0.5 to 2 times the volume of the reaction solution.

(Use)

The fluorine-containing ether compounds of the present invention have good compatibility with fluorine oil, etc. and are excellent in gelling ability. The compounds also have resistance to hydrolysis because they are ether compounds. They also have function of fluorine. Accordingly, they can be widely used as solvents, cosmetics, detergents, emulsifiers, surface finishing agents, lubricants, as well as lubricants or oils in the field of semiconductor/electronics. Further, the fluorine-containing ether compounds of the present invention are excellent in ability to gel organic solvents such as ethanol and oils such as ester oil, silicone oil, etc. used for cosmetics, particularly excellent in gelling ability for fluorine oils which are compounded, for example, in foundation. Accordingly, the fluorine-containing ether compounds of the present invention are particularly useful as gelling agents.

The present invention provides a method for gelling the aforementioned solvents or oils with the compounds according to the present invention.

In the present Invention the term, gelling, means that a treated material is solidfied, having been changed from the original liquid state.

The compound of the present invention is useful to solubilize and disperse a cosmetic preparation as a fluorinated oil or a fluorinated polymer.

(EXAMPLE)

The present invention will be illustrated in detail in the following examples, but the present invention should not be construed to be limited to them.

Example 1

Production of dodecyl{2-(perfluorooctyl}ethyl ether represented by the following formula (4):

$$CF_3(CF_2)_7-CH_2CH_2OCH_2CH_2CH_2CH_2CH_2CH_2CH_2CH_2CH_2CH_2CH_2CH_3 \quad (4)$$

2-(Perfluorooctyl)ethanol 13.9 g (0.03 mol), dodecylaldehyde 22.1 g (0.12 mol), 5% Pd-C (pH 6.8) 0.30 g as a catalyst, anhydrous magnesium sulfate 1.20 g (0.01 mol) as a dehydrating agent were charged in a 70 ml autoclave equipped with a hydrogen gas inlet and a stirrer, and stirring was conducted at 150° C. for 7 hours under hydrogen pressure of 10 kg/cm².

After reaction was completed, the catalyst and magnesium sulfate were removed by filtration, and an excess of dodecylaldehyde was removed under reduced pressure to provide the objective dodecyl{2-(perfluorooctyl)ethyl}ether 18.0 g (0.028 mol) as a colorless, transparent liquid. Isolation yield was 95%.

| ¹H-NMR | (δ: ppm, CDCl₃) |
|---|---|
| 0.70 | (triplet, 3H: a) |
| 0.90 ~ 1.25 | (broad singlet, 18H: b) |
| 1.25 ~ 1.50 | (complicated multiplet, 2H: c) |
| 2.05 ~ 2.44 | (complicated multiplet, 2H: d) |
| 3.26 | (triplet, 2H: e) |
| 3.52 | (triplet, 2H: f) | b.p. 130° C./0.4Torr
IR  C-H stretching vibration: 2932, 2860 cm⁻¹
    C-O-C stretching vibration: 1120 cm⁻¹
    CF₃ stretching vibration: 1050 ~ 1330, 68 ~ 760 cm⁻¹
    CF₂ stretching vibration: 1149 cm⁻¹

Example 2

Production of dodecyl(2-(perfluorodecyl)ethyl)ether represented by the following formula (5):

$$CF_3(CF_2)_9-CH_2CH_2OCH_2CH_2CH_2CH_2CH_2CH_2CH_2CH_2CH_2CH_2CH_2CH_3 \quad (5)$$

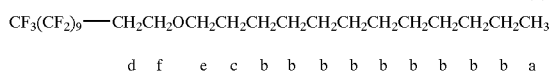

In the same manner as in Example 1, except that 2-(perfluorodecyl)ethanol 16.9 g (0.03 mol) was used instead of 2-(perfluorooctyl)ethanol and the amount of 5% Pd-C (pH 6.8) to be added was 0.34 g, reaction was carried out to obtain the objective dodecyl{2-(perfluorodecyl) ethyl}ether 21.1 g (0.029 mol) as a white solid. Isolation yield was 96%.

| ¹H-NMR | (δ: ppm, CDCl₃) |
|---|---|
| 0.70 | (triplet, 3H: a) |
| 0.90 ~ 1.25 | (broad singlet, 18H: b) |
| 1.27 ~ 1.50 | (complicated multiplet, 2H: c) |
| 2.05 ~ 2.40 | (complicated multiplet, 2H: d) |
| 3.28 | (triplet, 2H: e) |
| 3.54 | (triplet, 2H: f) | b.p. 149° C./0.4Torr
m.p. 40° C.
IR  C-H stretching vibration: 2932, 2860 cm⁻¹
    C-O-C stretching vibration: 1130 cm⁻¹
    CF₃ stretching vibration:
    1050 ~ 1330, 680 ~ 760 cm⁻¹
    CF₂ stretching vibration: 1152 cm⁻¹

Example 3

Production of dodecyl{2-(perfluorohexyl)ethyl}ether represented by the following formula (6):

$$CF_3(CF_2)_5-CH_2CH_2OCH_2CH_2CH_2CH_2CH_2CH_2CH_2CH_2CH_2CH_2CH_2CH_3 \quad (6)$$

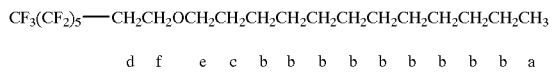

2-(Perfluorohexyl)ethanol 18.2 g (0.05 mol), 5% Pd-C (pH 7.2) 1.5 g as a catalyst were charged in a 70 ml autoclave equipped with a hydrogen gas inlet and a stirrer, to which was added dropwise dodecylaldehyde 13.8 g (0.075 mol) under atmospheric pressure over 6 hours and stirring was conducted at 105° C. for 8 hours while hydrogen was flowed continuously at 15 ml/min. After reaction was completed, the catalyst was removed by filtration, and an excess of dodecylaldehyde was removed under reduced pressure to provide the objective dodecyl{2-

(perfluorohexyl)ethyl}ether 25.3 g (0.048 mol) as a colorless, transparent liquid. Isolation yield was 95%.

| $^1$H-NMR | (δ: ppm, CDCl$_3$) | |
|---|---|---|
| | 0.70 | (triplet, 3H: a) |
| | 0.90 ~ 1.25 | (broad singlet, 18H: b) |
| | 1.25 ~ 1.50 | (complicated multiplet, 2H: c) |
| | 2.05 ~ 2.48 | (complicated multiplet, 2H: d) |
| | 3.25 | (triplet, 2H: e) |
| | 3.50 | (triplet, 2H: f) |
| b.p. 109° C./0.4Torr | | |
| IR | C-H stretching vibration: 2932, 2860 cm$^{-1}$ | |
| | C-O-C stretching vibration: 1090 cm$^{-1}$ | |
| | CF$_3$ stretching vibration: 1050 ~ 1330, 680 ~ 760 cm$^{-1}$ | |
| | CF$_2$ stretching vibration: 1146 cm$^{-1}$ | |

Example 4

Production of octadecyl{2-(perfluorodecyl)ethyl}ether represented by the following formula (7):

$$CF_3(CF_2)_9\text{———}CH_2CH_2OCH_2CH_2CH_2CH_2CH_2CH_2CH_2CH_2CH_2CH_2CH_2CH_2CH_2CH_2CH_2CH_2CH_3 \quad (7)$$

d   f   e   c   b   b   b   b   b   b   b   b   b   b   b   b   b   b   b   a 2-(Perfluorodecyl)ethanol 16.9 g (0.03 mol), 5% Pd-C (pH 7.2) 0.85 g as a catalyst were charged in a 70 ml autoclave equipped with a hydrogen gas inlet and a stirrer, to which was added dropwise octadecylaldehyde 12.1 g (0.045 mol) under hydrogen pressure of 1.5 kg/cm$^2$ over 6 hours and stirring was conducted at 150° C. for 9 hours while hydrogen was flowed continuously at 15 ml/min. After reaction was completed, the catalyst was removed by filtration, and an excess of octadecylaldehyde was removed under reduced pressure to provide the objective octadecyl{2-(perfluorodecyl)ethyl}ether 22.8 g (0.028 mol) as a white solid. Isolation yield was 93%.

| $^1$H-NMR | (δ: ppm, CDCl$_3$) | |
|---|---|---|
| | 0.80 | (triplet, 3H: a) |
| | 1.10 ~ 1.35 | (broad singlet, 30H: b) |
| | 1.35 ~ 1.60 | (complicated multiplet, 2H: c) |
| | 2.15 ~ 2.50 | (complicated multiplet, 2H: d) |
| | 3.38 | (triplet, 2H: e) |
| | 3.63 | (triplet, 2H: f) |
| m.p. 61° C. | | |
| IR | C-H stretching vibration: 2932, 2860 cm$^{-1}$ | |
| | C-O-C stretching vibration: 1130 cm$^{-1}$ | |
| | CF$_3$ stretching vibration: 1050 ~ 1330, 680 ~ 760 cm$^{-1}$ | |
| | CF$_2$ stretching vibration: 1152 cm$^{-1}$ | |

(Application Example)

Fluorine-containing ether compounds according to the present invention obtained in Examples 1 to 4 were evaluated for gelling ability with various organic solvents and oils according to the method shown below. In addition, the control samples 1 to 3 shown below were similarly evaluated for gelling ability.

The results are shown in Table 1.

<Method for evaluation of gelling ability>

Various fluorine-containing ether compounds were dissolved in solvents or oils at the concentration of 10% by weight, left at room temperature for one hour, and the conditions of the solution were visually observed.

<Control Sample>

Control sample 1: decyl{2-(perfluorooctyl)ethyl}ether
Control sample 2: ethyl{2-(perfluorohexyl)ethyl}ether
Control sample 3: perfluoropolyether (Trade name: Fomblin HC-04, manufactured by Audimont)

TABLE 1

| Fluorine-containing ether compound | Acetone | EtOH | Ester oil *1 | Silicone oil *2 | Fluorine oil *3 |
|---|---|---|---|---|---|
| Compound of example 1 | Dissolved | Dissolved | Gelled | Gelled | Gelled |
| Compound of example 2 | Dissolved | Gelled | Gelled | Gelled | Gelled |
| Compound of example 3 | Dissolved | Dissolved | Dissolved | Gelled | Not dissolved |
| Compound of example 4 | Gelled | Gelled | Gelled | Gelled | Gelled |

TABLE 1-continued

| Fluorine-containing ether compound | Acetone | EtOH | Ester oil *1 | Silicone oil *2 | Fluorine oil *3 |
|---|---|---|---|---|---|
| Control sample 1 | Dissolved | Dissolved | Dissolved | Dissolved | Not dissolved |
| Control sample 2 | Dissolved | Dissolved | Dissolved | Dissolved | Dissolved |
| Control sample 3 | Not dissolved | Not dissolved | Not dissolved | Not dissolved | — |

Note:
*1 ester oil: Estemol N-01, trade name of Nisshin Oil Mills
*2 silicone oil: SH200C-6cs, trade name of Toray Dow Corning Silicone
*3 fluorine oil: Fomblin HC-04, trade name of Audimont

What is claimed is:

1. A fluorine-containing ether compound represented by the formula (1):

$$Rf\text{—}(CH_2)_n\text{—}O\text{—}R^1 \quad (1)$$

wherein Rf represents a straight- or branched C$_{1-20}$ perfluoroalkyl or fluoroalkyl group, R$^1$ represents a straight or branched C$_{11-20}$ alkyl group, n is a number from 1 to 8.

2. A fluorine-containing ether compound according to claim 1, wherein Rf contains 4 to 20 carbon atoms and n is a number from 1 to 6.

3. A fluorine-containing ether compound according to claim 1, wherein Rf contains 8 to 20 carbon atoms and n is a number from 1 to 4.

4. A fluorine-containing ether compound according to claim 1, wherein n is 2.

5. A fluorine-containing ether compound according to claim 1, wherein Rf contains 10 to 20 carbon atoms.

6. A gelling agent which comprises a fluorine-containing ether compound according to claim 1.

7. A process for production of a fluorine-containing ether compound according to claim 1, which comprises reacting hydroxy compound, Rf—(CH$_2$)$_n$—OH, and carbonyl compound, $R^2$—(C=O)—$R^3$, in the presence of a catalyst in an atmosphere of hydrogen to obtain the ether compound.

8. A process according to claim 7, wherein the catalyst is selected from the group consisting of palladium, palladium hydroxide or palladium oxide supported on carbon, alumina, silica alumina, silica and zeolite.

9. A process according to claim 7, wherein the reaction is carried out while removing water which is a by-product of the reaction.

* * * * *